US011654055B2

(12) United States Patent
Chenegros et al.

(10) Patent No.: US 11,654,055 B2
(45) Date of Patent: May 23, 2023

(54) SENSORY SUBSTITUTION SYSTEM USING ASYNCHRONOUS TACTILE STIMULATION

(71) Applicants: SORBONNE UNIVERSITE, Paris (FR); CENTRE NATIONAL DE LA RECHERCHE SCIENTIFIQUE—CNRS, Paris (FR); INSERM (INSTITUT NATIONAL DE LA SANTÉ ET DE LA RECHERCHE MÉDICALE), Paris (FR)

(72) Inventors: Guillaume Chenegros, Trappes (FR); Ryad Benosman, Pantin (FR); Kevin Arth, Paris (FR); Sio-Hoi Ieng, Montreuil (FR)

(73) Assignees: SORBONNE UNIVERSITE, Paris (FR); CENTRE NATIONAL DE LA RECHERCHE SCIENTIFIQUE—CNRS, Paris (FR); INSERM (INSTITUT NATIONAL DE LA SANTE ET DE LA RECHERCHE MEDICALE), Paris (FR)

( * ) Notice: Subject to any disclaimer, the term of this patent is extended or adjusted under 35 U.S.C. 154(b) by 873 days.

(21) Appl. No.: 16/472,157

(22) PCT Filed: Dec. 7, 2017

(86) PCT No.: PCT/FR2017/053454
§ 371 (c)(1),
(2) Date: Jun. 20, 2019

(87) PCT Pub. No.: WO2018/115627
PCT Pub. Date: Jun. 28, 2018

(65) Prior Publication Data
US 2019/0332167 A1  Oct. 31, 2019

(30) Foreign Application Priority Data

Dec. 20, 2016 (FR) .................................. 16 62851

(51) Int. Cl.
| A41D 1/04 | (2006.01) |
| H04N 5/04 | (2006.01) |
| G06N 3/063 | (2023.01) |
| G06F 3/01 | (2006.01) |
| A41D 1/00 | (2018.01) |

(52) U.S. Cl.
CPC .............. *G06F 3/011* (2013.01); *A41D 1/002* (2013.01); *A41D 1/04* (2013.01); *G06F 3/016* (2013.01); *G06N 3/063* (2013.01); *H04N 5/04* (2013.01)

(58) Field of Classification Search
USPC ................................. 386/239, 242, 248, 277
See application file for complete search history.

(56) References Cited

U.S. PATENT DOCUMENTS 9,987,167 B2   6/2018  Lorach et al.
2007/0041600 A1  2/2007  Zachman
(Continued)

FOREIGN PATENT DOCUMENTS

CA    2 835 024 A1    11/2012
CN    103732287 A     4/2014
(Continued)

OTHER PUBLICATIONS

International search report (ISR), dated Mar. 14, 2018, from corresponding international application No. PCT/FR2017/053454.
(Continued)

*Primary Examiner* — Daquan Zhao
(74) *Attorney, Agent, or Firm* — Nixon & Vanderhye

(57) ABSTRACT

The sensory substitution system includes a portable matrix of exciters that can be worn by a user in such a way that the exciters are placed against the skin of a user, as well as a
(Continued)

control circuit for the exciters of the matrix. An asynchronous signal source provides the control circuit with an asynchronous signal representative of visual information organised according to a matrix of pixels. This asynchronous signal includes, for each pixel, successive events associated in an asynchronous manner with the pixel.

17 Claims, 4 Drawing Sheets

(56) References Cited

U.S. PATENT DOCUMENTS

| | | | |
|---|---|---|---|
| 2008/0135731 A1 | 6/2008 | Lichtsteiner et al. | |
| 2015/0366504 A1* | 12/2015 | Connor | A61B 5/6804 600/301 |
| 2017/0111619 A1* | 4/2017 | Benosman | G02C 11/10 |

FOREIGN PATENT DOCUMENTS

| | | | |
|---|---|---|---|
| CN | 106061456 A | 10/2016 | |
| JP | 2014-516665 A | 7/2014 | |
| WO | 2012153073 A1 | 11/2012 | |
| WO | 2013018090 A1 | 2/2013 | |
| WO | 2015100482 A1 | 7/2015 | |
| WO | WO-2015145017 A1 * | 10/2015 | A61B 5/6821 |
| WO | 2016/015099 A1 | 2/2016 | |

OTHER PUBLICATIONS

P. Bach-y-Rita : "Tactile sensory substitution studies", Annals of the New York Academy of Sciences, n° 1013, pp. 83-91.

D. Moraru, C.A. Boiangiu: "About Visual Sensory Substitution", Proceedings of the 3rd International Conference on Acoustics, Speech and Audio Processing (ASAP'15), Salerno, Italy, Jun. 2015, pp. 115-124.

C.C. Pack, S.J. Bensmaia: "Seeing and Feeling Motion: Canonical Computations in Vision and Touch", PLoS Biology, vol. 13, No. 9: e1002271, Sep. 2015.

P. Galambos: "Vibrotactile Feedback for Haptics and Telemanipulation: Survey, Concept and Experiment", Acta Polytechnica Hungarica, vol. 9, No. 1 (2012), pp. 41-65.

S. Maidenbaum, S. Abboud, A. Amedi: "Sensory substitution: Closing the gap between basic research and widespread practical visual rehabilitation", Neuroscience & Biobehavioral Reviews, vol. 41 (2014), pp. 3-15.

M. J. Berry, D.K. Warland, M. Meister: "The structure and precision of retinal spike trains". Proceedings of the National Academy of Sciences, vol. 94, No. 10 (1997), pp. 5411-5416.

P. Reinagel, R.C. Reid: "Temporal Coding of Visual Information in the Thalamus", The Journal of Neuroscience, vol. 20, No. 14 (2000), pp. 5392-5400.

C. Posch: "Bio-inspired vision", Journal of Instrumentation, vol. 7, No. 1 (2012), C01054.

P. Lichtsteiner, et al., "A 128×128 120 dB 15 microsecond Latency Asynchronous Temporal Contrast Vision Sensor", IEEE Journal of Solid-State Circuits, vol. 43, No. 2, Feb. 2008, pp. 566-576.

C. Posch, et al., "A QVGA 143 dB Dynamic Range Frame-Free PWM Image Sensor With Lossless Pixel-Level Video Compression and Time-Domain CDS", IEEE Journal of Solid-State Circuits, vol. 46, No. 1, Jan. 2011, pp. 259-275.

Office Action issued in Chinese Patent Application No. 201780086667.X dated Mar. 2, 2021.

Office Action issued in Japanese Patent Application No. 2019-533209 dated Jul. 27, 2020.

Office Action issued in Chinese Patent Application No. 201780086667.X dated Oct. 26, 2021.

* cited by examiner

SENSORY SUBSTITUTION SYSTEM USING ASYNCHRONOUS TACTILE STIMULATION

The present invention relates to sensory substitution systems and, in particular, those providing tactile stimuli for presenting visual information to users, in particular visually impaired users.

BACKGROUND

Retinal neuroprostheses are systems that stimulate the brain in order to make up for the lack of visual information in individuals suffering from sight loss.

These neuroprostheses are implanted invasively and electrically stimulate retinal cells upstream of the optic nerve. Operations to implant them and to then use them are expensive and may endanger the health of users, due to the necessary presence of a foreign body.

Genetic mutation solutions to make retinal cells photosensitive are also invasive because, once the mutation has taken place, it is impossible to reverse it.

Besides, such devices only function if the user's optic nerve is intact. Therefore, they neither help patients suffering from glaucoma nor those who are blind from birth. Ultimately, we are currently only at the early stages of cortical stimulation and research will still need time to perfect this type of application, which will be invasive in any case. These issues also affect various implantable neuroprostheses, such as an artificial ear or a tactile sensor for individuals with a loss of feeling and/or amputees.

To alleviate this problem, Bach-y-Rita conceived a device that stimulates the skin's natural receptors (P. Bach-y-Rita: "Tactile sensory substitution studies", Annals of the New York Academy of Sciences, no. 1013, pp. 83-91).

Sensory substitution devices of this type have proved successful in allowing patients to regain some of their independence. See D. Moraru, C. A. Boiangiu: "About Visual Sensory Substitution", Proceedings of the 3$^{rd}$ International Conference on Acoustics, Speech and Audio Processing (ASAP' 15), Salerno, Italy, June 2015, pp. 115-124, or C. C. Pack, S. J. Bensmaia: "Seeing and Feeling Motion: Canonical Computations in Vision and Touch", PLoS Biology, Vol. 13, No. 9: e1002271, September 2015.

However, known sensory substitution devices do not adequately meet the needs of blind individuals. They are generally bulky and power intensive, which reduces the benefit derived from their use. See P. Galambos: "Vibrotactile Feedback for Haptics and Telemanipulation: Survey, Concept and Experiment", Acta Polytechnica Hungarica, Vol. 9, No. 1 (2012), pp. 41-65, or S. Maidenbaum, S. Abboud, A. Amedi: "Sensory substitution: Closing the gap between basic research and widespread practical visual rehabilitation", Neuroscience & Biobehavioral Reviews, Vol. 41 (2014), pp. 3-15. In addition, they require a lengthy training period and their effectiveness depends greatly on the individual.

An object of the present invention is to propose another technique that is able to overcome the above difficulties, at least in part.

SUMMARY

The invention proposes a sensory substitution system, comprising: a matrix of exciters that can be worn by a user in such a way that the exciters interact locally with the skin, a control circuit for the exciters of the matrix and an asynchronous signal source for providing the control circuit with an asynchronous signal representative of visual information organised according to a matrix of pixels. The asynchronous signal comprises, for each pixel, successive events associated in an asynchronous manner with said pixel.

Such a sensory substitution system advantageously takes account of the functioning of the human brain and skin cells. The human body is able to receive asynchronous information on a millisecond scale. This allows it to optimally process information, as demonstrated by M. J. Berry, D. K. Warland, M. Meister: "The structure and precision of retinal spike trains", Proceedings of the National Academy of Sciences, Vol. 94, No. 10 (1997), pp. 5411-5416, and P. Reinagel, R. C. Reid: "Temporal Coding of Visual Information in the Thalamus", The Journal of Neuroscience, Vol. 20, No. 14 (2000), pp. 5392-5400.

Thanks to asynchronous signal sources such as neuromorphic cameras, it is possible to mimic the functioning of the eye, while greatly reducing the necessary processing of information.

This allows for reduced consumption of the sensory substitution system by tactile means and biomimicry of visual processing to be performed.

The proposed system allows the main drawbacks of sensory substitution systems, in terms of ergonomics, energy efficiency and adaptability to cellular functioning, to be addressed.

In one embodiment, the asynchronous signal source comprises a neuromorphic camera including photosensitive elements arranged according to a matrix of pixels facing a scene, with the asynchronous signal comprising, for each pixel, successive events originating in an asynchronous manner from said pixel.

The neuromorphic camera may, in particular, be of a DVS ("Dynamic Vision Sensor") or ATIS ("Asynchronous Time-based Image Sensor") type.

In another embodiment, the asynchronous signal source comprises a synthesizer producing a signal with an address-event representation (AER).

The asynchronous signal source may also include a memory where the asynchronous signal supplied to the control circuit is read.

According to one embodiment, the matrix of exciters is attached to a garment that can be worn by the user. This garment includes, for example, a vest. It may be made from a material having elasticity comprising, for example, neoprene.

In one embodiment of the sensory substitution system, the exciters of the matrix comprise mechanical actuators.

Alternatively, it is also possible that at least some of the exciters of the matrix are arranged to interact locally with the user's skin through stimulation, including electrical stimulation, heat variation, injection of a substance and application of an air flow.

BRIEF DESCRIPTION OF DRAWINGS

Other features and benefits of the present invention will appear in the following description of non-exhaustive examples of embodiments, with reference to the appended drawings, in which.

DESCRIPTION OF EMBODIMENTS

Figure 1:
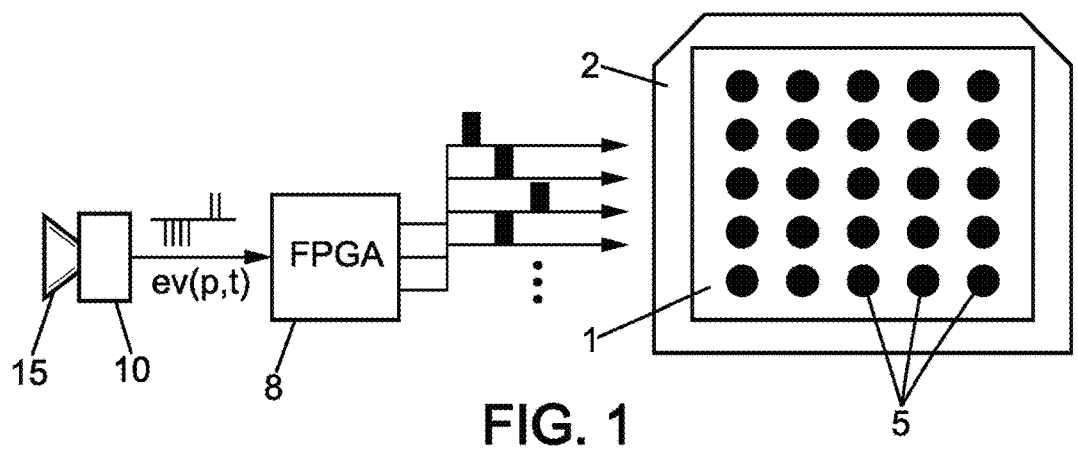
FIG. 1 is a block diagram of a sensory substitution system according to an embodiment of the invention.

With reference to FIG. 1, a sensory substitution system comprises a matrix of exciters 1 intended to be placed against the skin 2 of a user.

Each exciter 5 of the matrix 1 is placed such as to interact locally with the user's skin when it is activated by a control circuit 8.

In the example shown, the control circuit 8 is created using FPGA ("Field-Programmable Gate Array") technology. Other technologies may be used to create the control circuit 8, for example ASIC ("Application-Specific Integrated Circuit") technologies. The circuit 8 produces the respective control signals for the exciters 5 according to an asynchronous signal ev(p, t) received from a source 10.

The asynchronous signal ev(p, t) supplied to the control circuit 8 by the source 10 is representative of visual information organised according to a matrix of pixels. It consists of a stream of events, each with an address corresponding to a pixel p of the matrix and a time of occurrence t of the event.

By way of an example, the asynchronous signal source 10 may be a neuromorphic camera of the type described in the article by C. Posch: "*Bio-inspired vision*", Journal of Instrumentation, Vol. 7, No. 1 (2012), C01054.

FIG. 1 shows such a neuromorphic camera 10, constituting an event-based asynchronous vision sensor, placed facing a scene and receiving the luminous flux from the scene through an acquisition optic 15 comprising one or more lenses. The camera 10 is placed in the image plane of the acquisition optic. It comprises an array of photosensitive elements organised in a matrix of pixels. Each pixel corresponding to a photosensitive element produces successive events depending on light variations in the scene.

The asynchronous visual information from the camera 10 consists of sequences of events ev(p, t) received asynchronously from different pixels p according to light variations sensed by the pixel in the scene appearing in the camera's field of view.

Figure 2A:
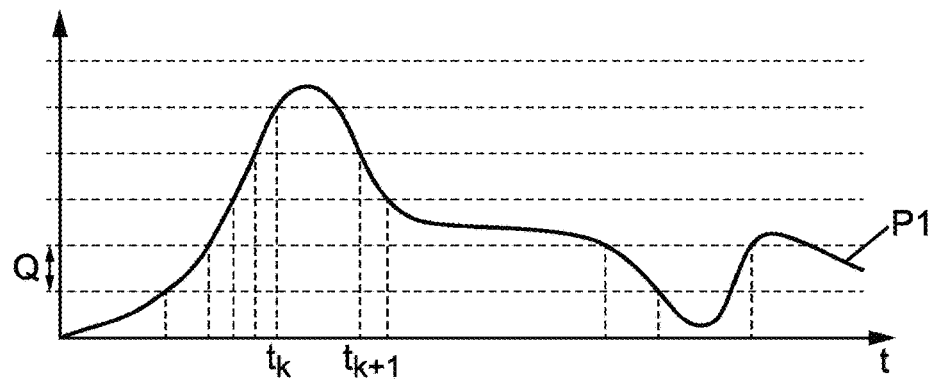
FIG. 2A is a diagram showing an example of a light intensity profile at a pixel of an asynchronous camera.
Figure 2B:
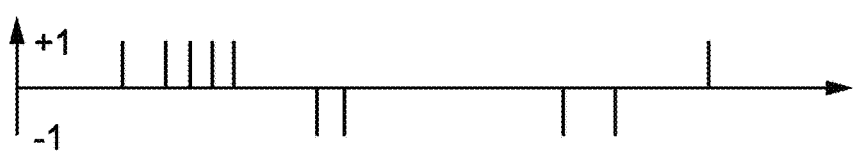
FIG. 2B shows an example of a signal produced by the asynchronous camera in response to the intensity profile in FIG. 2A.
Figure 2C:
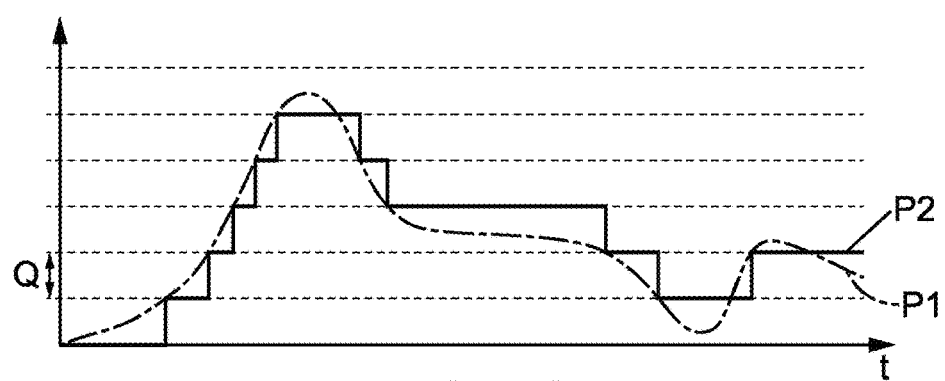
FIG. 2C illustrates the reconstruction of the intensity profile from the signal in FIG. 2B, FIGS. 3A-B are diagrams similar to those in FIGS. 2A-C illustrating a light acquisition mode that can be used in another exemplary embodiment of the method.

The asynchronous camera 10 effects an acquisition, for example according to the principle illustrated by FIGS. 2A-C. The information produced comprises a succession of moments $t_k$ (k=0, 1, 2, etc.) at which an activation threshold Q is reached. FIG. 2A shows an example of a light intensity profile P1 seen by a pixel of the matrix. Each time this intensity increases by an amount equal to the activation threshold Q from what it was at the time $t_k$, a new moment $t_{k+1}$ is identified and a positive ray (level +1 in FIG. 2B) is transmitted at this moment $t_{k+1}$. Symmetrically, each time that the intensity of the pixel decreases by the quantity Q from what it was at the time $t_k$, a new moment $t_{k+1}$ is identified and a negative ray (level −1 in FIG. 2B) is transmitted at this moment $t_{k+1}$. Therefore, the asynchronous signal sequence for the pixel consists of a succession of positive or negative pulses or rays ("spikes") positioned in time at moments $t_k$ according to the light profile for the pixel. These rays can be represented mathematically by positive or negative Dirac spikes and each characterised by a transmission moment $t_k$ and a sign bit. Therefore, the output from the camera 10 takes the form of an address-event representation (AER). FIG. 2C shows the intensity profile P2 that can be reconstructed as an approximation of the profile P1 by temporal integration of the asynchronous signal in FIG. 2B.

Figure 3A:
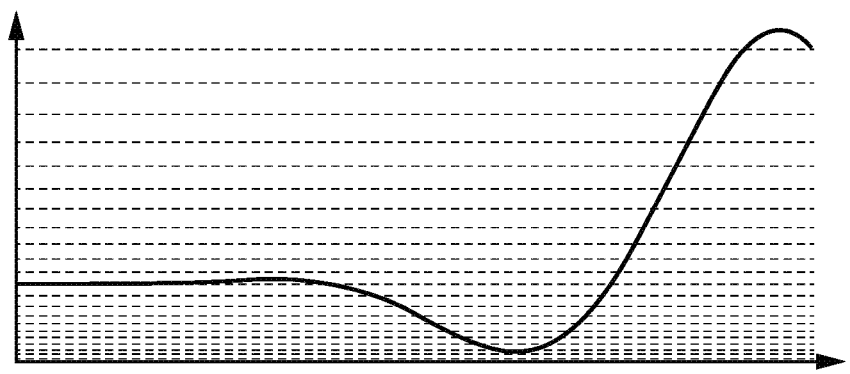
Figure 3B:
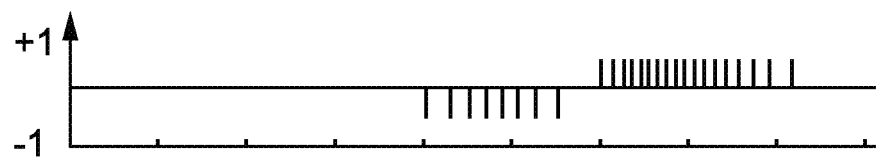

The activation threshold Q may be fixed, as is the case in FIGS. 2A-C, or adaptive according to light intensity, as is the case in FIGS. 3A-B. For example, the threshold ±Q can be compared with variations in the light intensity logarithm for generating an event ±1.

By way of an example, the asynchronous camera 10 may be a dynamic vision sensor (DVS) of the type described in "*A 128×128 120 dB 15 µs Latency Asynchronous Temporal Contrast Vision Sensor*", P. Lichtsteiner, et al., IEEE Journal of Solid-State Circuits, Vol. 43, No. 2, February 2008, pp. 566-576, or in the patent application US 2008/0135731 A1. It is possible to come close to the dynamics of a retina (minimum time between action potentials) of around a few milliseconds with a DVS of this type. In any event, the dynamic performance is broadly superior to that which can be achieved with a conventional video camera with a realistic sample rate. It should be noted that the form of the asynchronous signal produced for a pixel by the DVS 10, which constitutes the input signal for the control circuit 8, may differ from a succession of Dirac spikes, with it being possible for the events represented to have a temporal width or an amplitude or a wave form of any kind in this event-based asynchronous signal.

Another example of an asynchronous camera, which may be of beneficial use within the framework of the present invention, is the asynchronous time-based image sensor (ATIS), a description of which is provided in the article "*A QVGA 143 dB Dynamic Range Frame-Free PWM Image Sensor With Lossless Pixel-Level Video Compression and Time-Domain CDS*", C. Posch, et al., IEEE Journal of Solid-State Circuits, Vol. 46, No. 1, January 2011, pp. 259-275.

Figure 4:
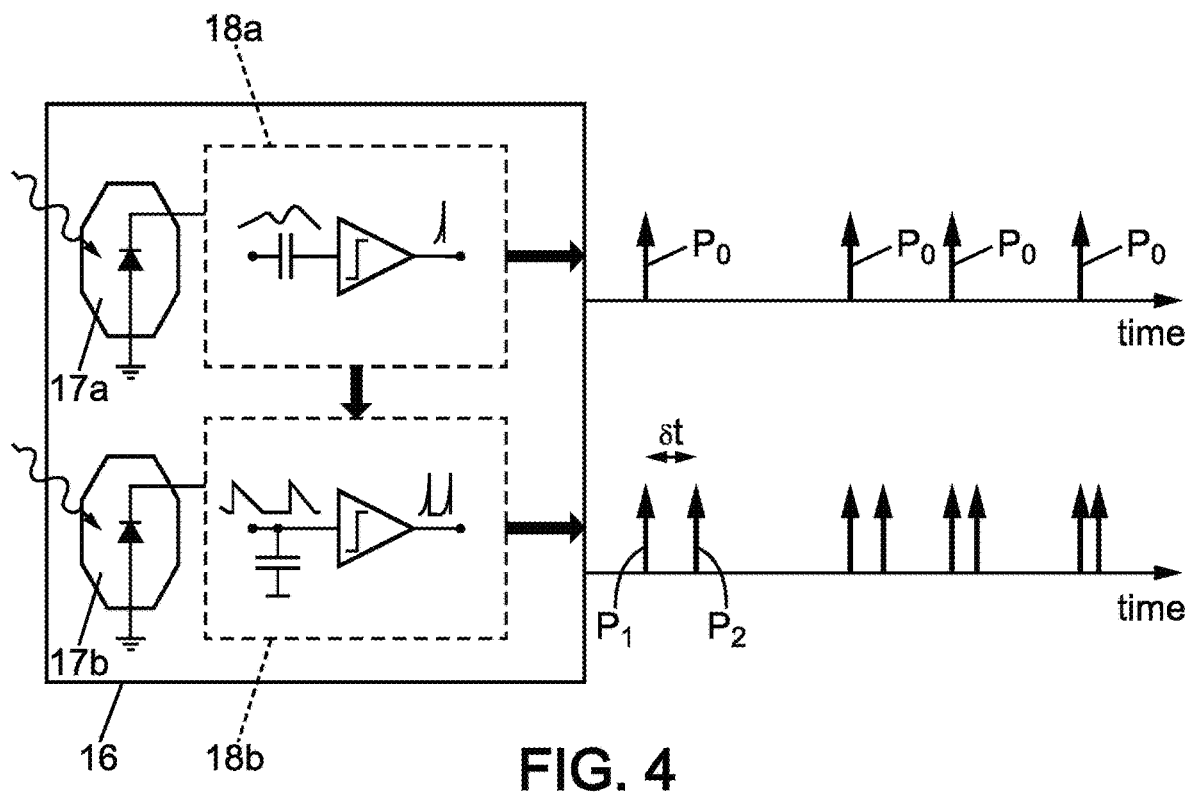
FIG. 4 is a block diagram of an ATIS type asynchronous camera.

FIG. 4 illustrates the principle of the ATIS. A pixel 16 of the matrix constituting the camera comprises two photosensitive elements 17a, 17b, such as photodiodes, associated respectively with electronic detection circuits 18a, 18b. The sensor 17a and its circuit 18a function in a similar way to the aforementioned DVS. They produce a pulse $P_0$ when the light intensity received by the photodiode 17a varies by a predetermined amount. The pulse $P_0$ marking this change in intensity triggers the electronic circuit 18b associated with the other photodiode 17b. This circuit 18b then generates a first pulse $P_1$ followed by a second pulse $P_2$ as soon as a given amount of light (number of photons) is received by the photodiode 17b. The time gap St between the pulses $P_1$ and $P_2$ is inversely proportional to the light intensity received by the pixel 16 just after the occurrence of the pulse $P_0$. The asynchronous information from the ATIS is another form of AER representation, comprising two pulse trains for each pixel: the first pulse train $P_0$ indicates the moments when the light intensity has changed beyond the detection threshold, while the second train comprises pulses $P_1$ and $P_2$, the time gap St for which indicates the corresponding light intensities, or grey scales. Therefore, an event ev(p, t) originating from a pixel 16 with position p in the matrix of the ATIS comprises two types of information: time information provided by the position of the pulse $P_0$, providing the moment t of the event, and grey scale information provided by the time gap St between the pulses $P_1$ and $P_2$.

In another embodiment, the asynchronous signal source 10 that supplies the control circuit 8 is not a camera observing an actual scene, but a signal synthesizer with an address-event representation (AER). The asynchronous signal v(p, t) is synthesized by such a source such as to emulate the images to be presented to the user, which may be more or less realistic, or even abstract.

For example, the images presented in this way by the sensory substitution system may correspond to elements of a graphical user interface (GUI) of the type commonly used in various devices such as smartphones, tablets, computers, televisions, etc. The asynchronous signal produced by the synthesizer may result from a conversion of standard format graphic elements, or be generated directly to satisfy the requirements of the sensory substitution system.

The asynchronous signal source 10 may also function by reading from a memory, of an electronic, magnetic or optical type, to supply the control circuit 8 with an event-based asynchronous signal, which has previously been recorded after having been acquired using either a neuromorphic camera or a synthesizer.

The control circuit 8 supplies the exciters 5 of the matrix 1 from the asynchronous signal received from the source 10. Each exciter 5 receives an individual command in the form of a supply voltage provided selectively when events are received for pixels with corresponding positions in the address-event representation (AER).

Each exciter 5 of the matrix 1 may consist of a mechanical actuator, for example, of a piezoelectric type, which creates vibration and/or pressure on the skin 2 when activated by its respective signal originating from the control circuit 8.

Other types of stimulation may also be applied locally by an exciter 5 of the matrix 1:
  electrical stimulation using electrodes selectively supplied with a voltage by the control circuit 8,
  heat variation using a thermal device,
  injection of a substance,
  application of an air flow, etc.

A combination of exciters 5 of different types within the matrix 1 is also conceivable. What matters is the local nature of the excitation applied by each element 5 of the matrix 1. This matrix thus makes it possible to provide a kind of map of excitation points on the user's skin, which produces a spatial perception diagram facilitating sensory substitution.

It is possible that the spatial density of exciters 5 in the matrix 1 is lower than that of pixels used to acquire the asynchronous signal. In this case, the control circuit 8 may perform spatial integration to produce the control signals for the exciters 5.

It is also possible to interface any kind of system generating information in an asynchronous manner, including non-visual systems. For example, provision may be made of an asynchronous low pressure sensor for amputees, or even of an asynchronous audio device. Therefore, the use of sensory substitution devices may encompass any kind of sensor enabling information to be provided in the form of event streams.

To simplify the connection of exciters 5, it is possible to arrange the matrix 1 such that it presents a common ground plane for all of the exciters or some of them. In this case, it is sufficient to supply the control voltage for each exciter 5 via a wire or a conductive track. The ground plane may, in particular, take the form of a conductive textile sheet 20 connected to a power supply terminal associated with the control circuit 8, and to which the exciters 5 are attached.

Figure 5:
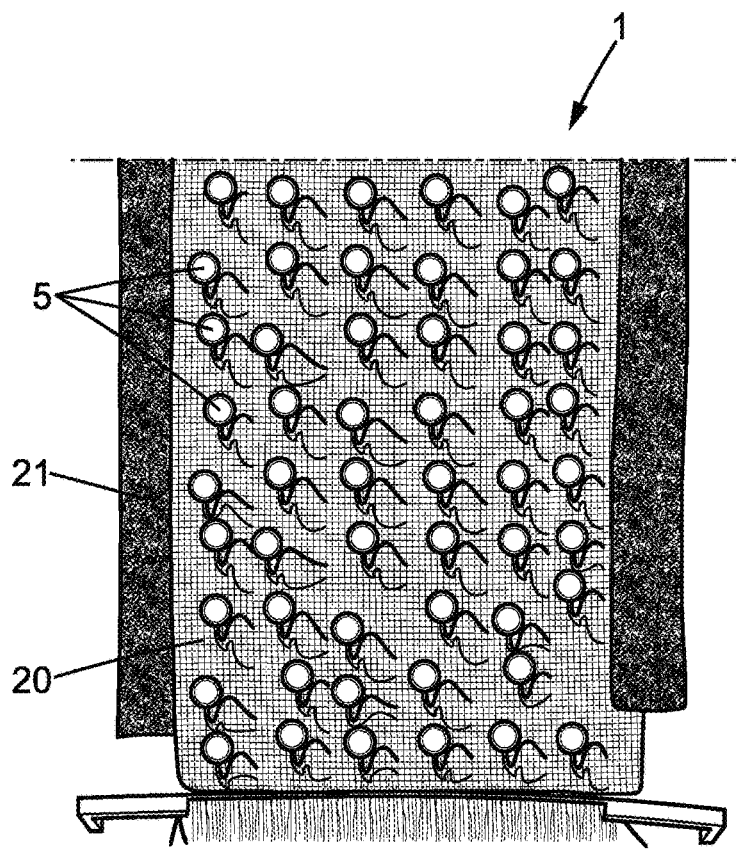
FIG. 5 is a schematic view of a matrix of exciters that can be used in certain embodiments of the invention.

FIG. 5 shows such a textile sheet 20 on which the exciters 5, in this example, made up of mechanical actuators 5, are installed. In this example, the sheet 20 is stitched or glued to another textile backing 21 intended to come into contact with the user's skin 2, in order to convey to the latter the pressure or vibration created by the actuators 5.

Figure 6:
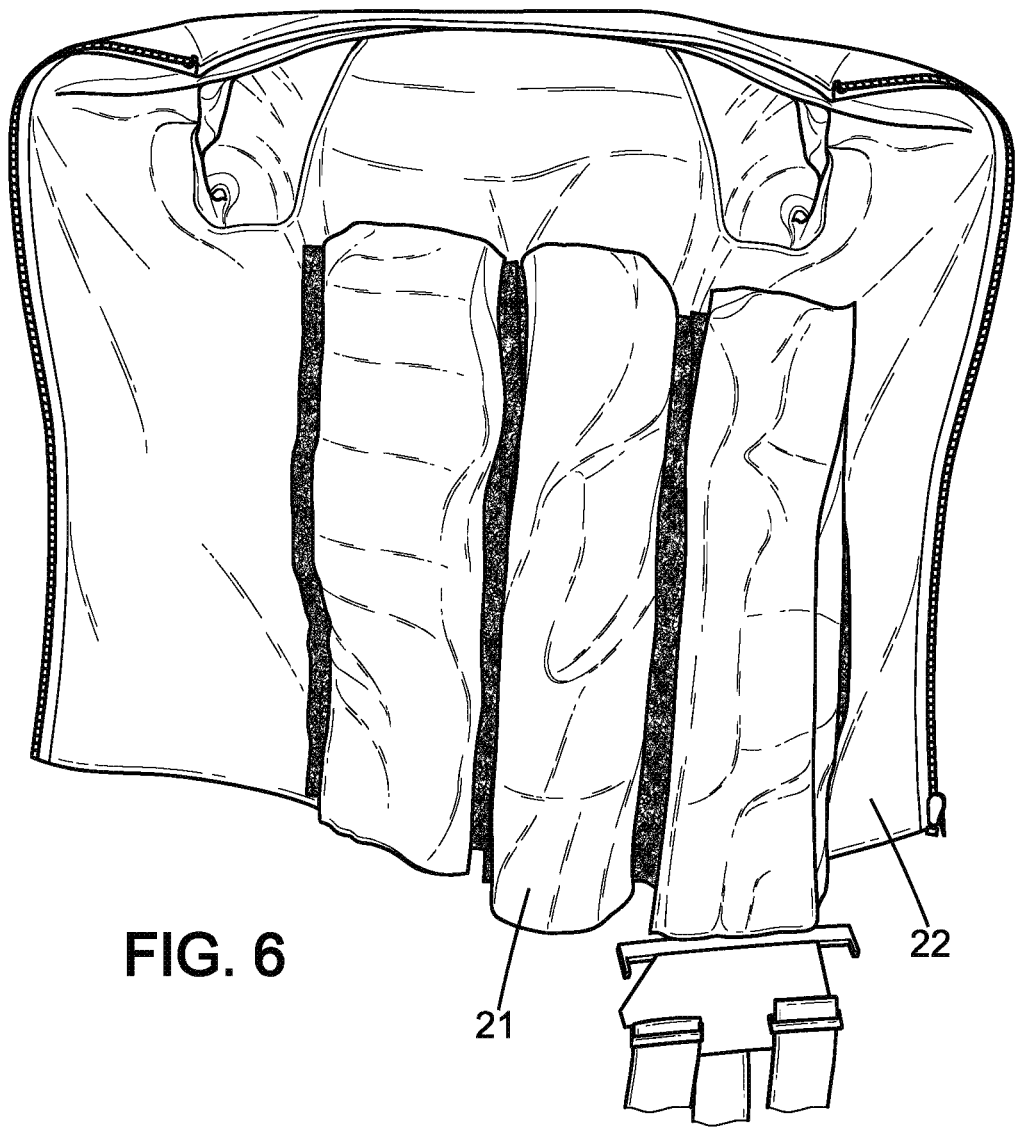
FIG. 6 shows a garment equipped with such a matrix of exciters.

As shown in FIG. 6, the assembly comprising the matrix of actuators 1 and the backing 21 may be attached to the inside of a garment 22 that can be worn by the user such that the backing 21 lies against the user's skin, in order to create the desired mechanical coupling with the actuators 5.

The garment 22 is preferably made from a material having elasticity, in order to properly apply the matrix of actuators 1 against the user's skin 2. By way of example, the garment 22 may be made from neoprene. Typically, it may be a vest, such that the matrix of actuators 1 is placed against the user's back or possibly his/her sides, and possibly his/her stomach. As shown in FIG. 6, the actuators 5 may be spread across several subassemblies to reduce the overall rigidity of the equipped garment.

Of course, the matrix 1 may comprise exciters 5 distributed across other parts of the user's body, in particular the limbs. The garment to which it is attached may be a suit covering more than the user's torso.

The above-described sensory substitution system takes account of the functioning of the skin's receptor cells from the point of view of the spatiotemporal interpretation performed by the brain. It is thus able to generate tactile, electrical, physical or other stimuli asynchronously in different areas of the body.

The exciters 5 are distributed such that they match the density of receptor cells in the stimulated area.

The visual information communicated with sensory substitution may be spaced a few microseconds apart. The supply voltages for the exciters 5 have pulses that last for the time needed to stimulate the receptor cells with the desired intensity. A wide range of stimulation strategies may be implemented depending on the nature of the information to be transmitted. It is possible, in particular, to simulate the different grey scales of an image, or even to simulate the writing in a text for word recognition.

Tests have been performed on healthy subjects, in order to study their responses to such stimuli. These tests, performed with mechanical actuators 5 in the matrix 1, have provided very encouraging results. After a few minutes of training, the recognition of letters and numbers, as well as various geometric shapes, was already satisfactory. These tests also allowed the high-speed movement of objects in the field of view of the neuromorphic camera 10, as described above, to be identified. This is an extremely promising result in view of other dynamic mobility experiments. Individuals' idiosyncrasies can also be taken into account, in order to be able to interface the system with each subject.

The above-described embodiments are a simple illustration of the present invention. They can be modified in various ways without departing from the scope of the invention, which is apparent from the appended claims.

The invention claimed is:

1. A sensory substitution system, comprising:
   a matrix of exciters configured to be worn by a user such that the exciters interact locally with the skin of the user, the matrix of exciters comprising mechanical actuators;
   a control circuit configured to control the exciters of the matrix; and an asynchronous signal source configured to provide the control circuit with an asynchronous signal representative of visual information organized according to a matrix of pixels, the asynchronous signal comprising, for each of the pixels, successive events associated in an asynchronous manner with said pixel, wherein the matrix of exciters produces a spatial tactile perception diagram representative of the visual information.

2. The system as claimed in claim 1, wherein the asynchronous signal source comprises a neuromorphic camera including photosensitive elements disposed according to the matrix of pixels facing a scene, the asynchronous signal comprising, for each of the pixels, the successive events originating in the asynchronous manner from said pixel.

3. The system as claimed in claim 2, wherein the neuromorphic camera is one of a Dynamic Vision Sensor and an Asynchronous Time-based Image Sensor.

4. The system as claimed in claim 3, wherein the matrix of exciters is attached to a garment configured to be worn by the user.

5. The system as claimed in claim 2, wherein the matrix of exciters is attached to a garment configured to be worn by the user.

6. The system as claimed in claim 1, wherein the asynchronous signal source comprises a synthesizer producing a signal with an address-event representation.

7. The system as claimed in claim 6, wherein the matrix of exciters is attached to a garment configured to be worn by the user.

8. The system as claimed in claim 1, wherein the asynchronous signal source comprises a memory where the asynchronous signal supplied to the control circuit is read.

9. The system as claimed in claim 8, wherein the matrix of exciters is attached to a garment configured to be worn by the user.

10. The system as claimed in claim 1, wherein the matrix of exciters is attached to a garment configured to be worn by the user.

11. The system as claimed in claim 10, wherein the garment includes a vest.

12. The system as claimed in claim 11, wherein the garment is made from a material having elasticity.

13. The system as claimed in claim 10, wherein the garment is made from a material having elasticity.

14. The system as claimed in claim 13, wherein the material having elasticity comprises neoprene.

15. The system as claimed in claim 1, wherein at least some of the exciters of the matrix are disposed to interact locally with the skin of the user through stimulation, including electrical stimulation, heat variation, injection of a substance, and application of an air flow.

16. A sensory substitution system, comprising:
a matrix of exciters configured to be worn by a user such that the exciters interact locally with the skin of the user, the matrix of exciters being attached to a garment configured to be worn by the user, the garment including a vest;
a control circuit configured to control the exciters of the matrix; and
an asynchronous signal source configured to provide the control circuit with an asynchronous signal representative of visual information organized according to a matrix of pixels, the asynchronous signal comprising, for each of the pixels, successive events associated in an asynchronous manner with said pixel,
wherein the matrix of exciters produces a spatial tactile perception diagram representative of the visual information.

17. The system as claimed in claim 16, wherein the exciters of the matrix comprise mechanical actuators.

* * * * *